(12) United States Patent
Brace et al.

(10) Patent No.: US 6,342,057 B1
(45) Date of Patent: Jan. 29, 2002

(54) REMOTELY ALIGNED SURGICAL DRILL GUIDE

(75) Inventors: Michael Brace, Lansdale; Roger Berger, Wayne; Hansjuerg W. Emch, Philadelphia, all of PA (US)

(73) Assignee: Synthes (USA), Paoli, PA (US)

( * ) Notice: Subject to any disclaimer, the term of this patent is extended or adjusted under 35 U.S.C. 154(b) by 0 days.

(21) Appl. No.: 09/560,896

(22) Filed: Apr. 28, 2000

(51) Int. Cl.[7] ................................................ A61B 17/56
(52) U.S. Cl. .......................................................... 606/96
(58) Field of Search ............................. 606/53, 86, 80, 606/96, 98, 104, 69, 70, 71

(56) References Cited

U.S. PATENT DOCUMENTS

| | | | |
|---|---|---|---|
| 1,831,813 A | 11/1931 | Levedahl |
| 2,200,120 A | 5/1940 | Nauth |
| 2,235,419 A | 3/1941 | Callahan et al. |
| 2,248,054 A | 7/1941 | Becker |
| 2,267,157 A | 12/1941 | Lippincott |
| 2,490,364 A | 12/1949 | Livingston |
| 2,494,229 A | 1/1950 | Collison |
| 2,500,370 A | 3/1950 | McKibbin |
| 2,839,953 A | 6/1958 | Hanger |
| 2,935,905 A | 5/1960 | Winslow |
| 3,244,170 A | 4/1966 | McElvenny |
| 3,530,860 A | 9/1970 | Majoros |
| 3,664,022 A | 5/1972 | Small |
| 3,704,707 A | 12/1972 | Halloran |

(List continued on next page.)

FOREIGN PATENT DOCUMENTS

| | | |
|---|---|---|
| DE | 36 17 207 A1 | 11/1987 |
| DE | 41 09 440 A1 | 4/1992 |
| DE | 42 38 582 A1 | 5/1994 |
| DE | 198 28 137 A1 | 1/2000 |
| EP | 0 153 831 A2 | 9/1985 |
| EP | 0 201 011 A2 | 11/1986 |
| EP | 0 240 004 A2 | 10/1987 |
| EP | 0 307 241 A2 | 3/1989 |
| EP | 0 460 447 A1 | 12/1991 |
| EP | 0 495 488 A2 | 7/1992 |
| EP | 0 518 071 A1 | 12/1992 |
| EP | 0 633 748 B1 | 3/1998 |
| EP | 0 880 938 A1 | 12/1998 |
| EP | 0 683 651 B1 | 9/1999 |
| FR | 2 700 462 | 7/1994 |
| FR | 2 718 014 | 10/1995 |
| GB | 2 243 316 A | 10/1991 |
| JP | 9075366 | 3/1997 |
| WO | WO 94/15556 | 7/1994 |
| WO | WO 98/34569 | 8/1998 |
| WO | Wo 99/59481 | 11/1999 |

OTHER PUBLICATIONS

*Synthes Maxillofacial*, catalog, 9/97, pp. 3–9, 3–30, 3–33, 3–34, 3–35, 3–40, and 4–27.
*Synthes Spine*, catalog, 1/98, pp. 1–3, 1–46, 1–70, 1–71, 3–2, 3–6, 3–18, 3–19, and 3–21.
*Synthes* catalog, 3/97, pp. 3–15, 3–16, 3–17, 3–18, 3–19, 3–30, 3–31, 3–38, 3–83, 3–89, and 3–90.
*Stryker Implants*; Equinox Cervical Compression & Monobloc Anterior Plate System, undated.

(List continued on next page.)

*Primary Examiner*—Eduardo C. Robert
(74) *Attorney, Agent, or Firm*—Pennie & Edmonds LLP

(57) ABSTRACT

A surgical drill guide assembly for demountable attachment to a slotted bone plate is provided. The drill guide assembly includes one or more alignment drill tubes that are remotely aligned with corresponding fastener holes in the bone plate, and an expandable bushing that is configured and dimensioned to engage a slot in the bone plate. A variable angle block permits angulation of the alignment drill tubes about a central axis of the surgical drill guide assembly. The alignment drill tubes are releasably lockable at a surgeon-selected angle.

20 Claims, 9 Drawing Sheets

U.S. PATENT DOCUMENTS

| | | |
|---|---|---|
| 3,727,611 A | 4/1973 | Schultz |
| 3,760,802 A | 9/1973 | Fischer et al. |
| 3,765,034 A | 10/1973 | Johnston |
| 3,814,089 A | 6/1974 | Deyerle |
| 3,867,932 A | 2/1975 | Huene |
| 3,892,232 A | 7/1975 | Neufeld |
| 3,895,444 A | 7/1975 | Small |
| 4,119,092 A | 10/1978 | Gil |
| 4,251,216 A | 2/1981 | Weissman |
| 4,253,784 A | 3/1981 | Anderson |
| 4,312,337 A | 1/1982 | Donohue |
| 4,325,373 A | 4/1982 | Slivenko et al. |
| 4,341,206 A | 7/1982 | Perrett et al. |
| 4,360,012 A | 11/1982 | McHarrie et al. |
| 4,383,527 A | 5/1983 | Asnis et al. |
| 4,399,813 A | 8/1983 | Barber |
| 4,409,973 A | 10/1983 | Neufeld |
| 4,450,835 A | 5/1984 | Asnis et al. |
| 4,465,065 A | 8/1984 | Gotfried |
| 4,502,475 A | 3/1985 | Weigle et al. |
| 4,522,201 A | 6/1985 | Tongue |
| 4,528,980 A | 7/1985 | Kenna |
| 4,537,185 A | 8/1985 | Stednitz |
| 4,541,424 A | 9/1985 | Grosse et al. |
| 4,549,538 A | 10/1985 | Schadrack, III et al. |
| 4,570,624 A | 2/1986 | Wu |
| 4,586,497 A | 5/1986 | Dapra et al. |
| 4,599,999 A | 7/1986 | Klaue |
| 4,608,972 A | 9/1986 | Small |
| 4,612,922 A | 9/1986 | Barber |
| 4,686,972 A | 8/1987 | Kurland |
| 4,708,139 A | 11/1987 | Dunbar, IV |
| 4,713,077 A | 12/1987 | Small |
| 4,714,469 A | 12/1987 | Kenna |
| 4,716,893 A | 1/1988 | Fischer et al. |
| 4,733,654 A | 3/1988 | Marino |
| 4,738,255 A | 4/1988 | Goble et al. |
| 4,744,353 A | 5/1988 | McFarland |
| 4,747,400 A | 5/1988 | Koeneman et al. |
| 4,760,843 A | 8/1988 | Fischer et al. |
| 4,787,377 A | 11/1988 | Laboureau |
| 4,788,970 A | 12/1988 | Kara et al. |
| 4,798,213 A | 1/1989 | Doppelt |
| 4,813,407 A | 3/1989 | Vogen |
| 4,823,780 A | 4/1989 | Odensten et al. |
| 4,834,080 A | 5/1989 | Brown |
| 4,848,327 A | 7/1989 | Perdue |
| 4,852,558 A | 8/1989 | Outerbridge |
| 4,865,025 A | 9/1989 | Buzzi et al. |
| 4,881,535 A | 11/1989 | Sohngen |
| 4,903,691 A | 2/1990 | Heinl |
| 4,907,577 A | 3/1990 | Wu |
| 4,911,153 A | 3/1990 | Border |
| 4,917,604 A | 4/1990 | Small |
| 4,978,351 A | 12/1990 | Rozas |
| 5,002,547 A | 3/1991 | Poggie et al. |
| 5,026,373 A | 6/1991 | Ray et al. |
| 5,026,375 A | 6/1991 | Linovitz et al. |
| 5,026,376 A | 6/1991 | Greenberg |
| 5,030,219 A | 7/1991 | Matsen, III et al. |
| 5,047,034 A | 9/1991 | Sohngen |
| 5,112,336 A | 5/1992 | Krevolin et al. |
| 5,112,337 A | 5/1992 | Paulos et al. |
| 5,133,720 A | 7/1992 | Greenberg |
| 5,139,520 A | 8/1992 | Rosenberg |
| 5,141,513 A | 8/1992 | Fortune et al. |
| 5,147,367 A | 9/1992 | Ellis |
| 5,151,103 A | 9/1992 | Tepic et al. |
| 5,154,721 A | 10/1992 | Perez |
| 5,176,681 A | 1/1993 | Lawes et al. |
| 5,180,384 A | 1/1993 | Mikhail |
| 5,180,388 A | 1/1993 | DiCarlo |
| 5,207,682 A | 5/1993 | Cripe |
| 5,207,753 A | 5/1993 | Badrinath |
| 5,250,055 A | 10/1993 | Moore et al. |
| 5,306,278 A | 4/1994 | Dahl et al. |
| 5,320,626 A | 6/1994 | Schmieding |
| 5,324,295 A | 6/1994 | Shapiro |
| 5,346,496 A | 9/1994 | Pennig |
| 5,350,380 A | 9/1994 | Goble et al. |
| 5,354,300 A | 10/1994 | Goble et al. |
| 5,364,399 A | 11/1994 | Lowery et al. |
| 5,366,457 A | 11/1994 | McGuire et al. |
| 5,403,322 A | 4/1995 | Herzenberg et al. |
| 5,409,329 A | 4/1995 | Juang |
| 5,409,493 A | 4/1995 | Greenberg |
| 5,423,826 A | 6/1995 | Coates et al. |
| 5,425,490 A | 6/1995 | Goble et al. |
| 5,429,641 A | 7/1995 | Gotfried |
| 5,437,677 A | 8/1995 | Shearer et al. |
| 5,458,602 A | 10/1995 | Goble et al. |
| 5,462,549 A | 10/1995 | Glock |
| 5,474,559 A | 12/1995 | Bertin et al. |
| 5,478,341 A | 12/1995 | Cook et al. |
| 5,489,210 A | 2/1996 | Hanosh |
| 5,507,801 A | 4/1996 | Gisin et al. |
| 5,514,144 A | 5/1996 | Bolton |
| 5,520,690 A | 5/1996 | Errico et al. |
| 5,531,746 A | 7/1996 | Errico et al. |
| 5,531,751 A | 7/1996 | Schultheiss et al. |
| 5,562,735 A | 10/1996 | Margulies |
| 5,584,838 A | 12/1996 | Rona et al. |
| 5,584,839 A | 12/1996 | Gieringer |
| 5,601,550 A | 2/1997 | Esser |
| 5,613,970 A | 3/1997 | Houston et al. |
| 5,620,449 A | 4/1997 | Faccioli et al. |
| 5,632,747 A | 5/1997 | Scarborough et al. |
| 5,634,927 A | 6/1997 | Houston et al. |
| 5,637,112 A | 6/1997 | Moore et al. |
| 5,641,287 A | 6/1997 | Gittleman |
| 5,643,274 A | 7/1997 | Sander et al. |
| 5,649,930 A | 7/1997 | Kertzner |
| 5,665,086 A | 9/1997 | Itoman et al. |
| 5,669,915 A | 9/1997 | Caspar et al. |
| 5,676,666 A | 10/1997 | Oxland et al. |
| 5,676,667 A | 10/1997 | Hausman |
| 5,683,400 A | 11/1997 | McGuire |
| 5,697,933 A | 12/1997 | Gundlapalli et al. |
| 5,713,905 A | 2/1998 | Goble et al. |
| 5,725,532 A | 3/1998 | Shoemaker |
| 5,743,916 A | 4/1998 | Greenberg et al. |
| 5,746,743 A | 5/1998 | Greenberg |
| 5,755,721 A | 5/1998 | Hearn |
| 5,766,179 A | 6/1998 | Faccioli et al. |
| 5,769,856 A | 6/1998 | Dong et al. |
| 5,800,551 A | 9/1998 | Williamson et al. |
| 5,817,098 A | 10/1998 | Albrektsson et al. |
| 5,833,693 A | 11/1998 | Abrahami |
| 5,836,950 A | 11/1998 | Hansson |
| RE36,020 E | 12/1998 | Moore et al. |
| 5,851,207 A | 12/1998 | Cesarone |
| 5,860,980 A | 1/1999 | Axelson, Jr. et al. |
| 5,885,300 A | 3/1999 | Tokuhashi et al. |
| 5,888,034 A | 3/1999 | Greenberg |
| 5,891,150 A | 4/1999 | Chan |
| 5,895,389 A | 4/1999 | Schenk et al. |
| 5,899,908 A | 5/1999 | Kuslich et al. |
| 5,904,685 A | 5/1999 | Walawalkar |
| 5,910,143 A | 6/1999 | Cripe et al. |
| 5,935,128 A | 8/1999 | Carter et al. |
| 5,938,686 A | 8/1999 | Benderev et al. |

| | | |
|---|---|---|
| 5,951,561 A | 9/1999 | Pepper et al. |
| 5,954,722 A * | 9/1999 | Bono .......................... 606/70 |
| 5,954,769 A | 9/1999 | Rosenlicht |
| 5,961,530 A | 10/1999 | Moore et al. |
| 6,007,535 A | 12/1999 | Rayhack et al. |
| 6,010,509 A | 1/2000 | Delgado et al. |
| 6,013,083 A | 1/2000 | Bennett |
| 6,033,409 A | 3/2000 | Allotta |
| 6,036,695 A | 3/2000 | Smith |
| 6,059,789 A | 5/2000 | Dinger et al. |
| 6,066,142 A | 5/2000 | Serbousek et al. |
| 6,079,681 A | 6/2000 | Stern et al. |
| 6,210,415 B1 * | 4/2001 | Bester .......................... 606/96 |
| 6,235,034 B1 * | 5/2001 | Bray ........................... 606/71 |

OTHER PUBLICATIONS

*Stryker Implants*; Equinox Cervical Compression & Monobloc Anterior Plate System: Surgical Technique, undated.

*Blackstone Medical Inc.*, Blackstone Anterior Cervical Plate, undated.

*Synthes Spine* Cervical Spine Locking Plate System: The Standard, 1995.

*Synthes Spine* Cervical Spine Locking Plate System: New Additions, 1995.

*Synthes Spine* Cervical Spine Locking Plate, 1991.

* cited by examiner

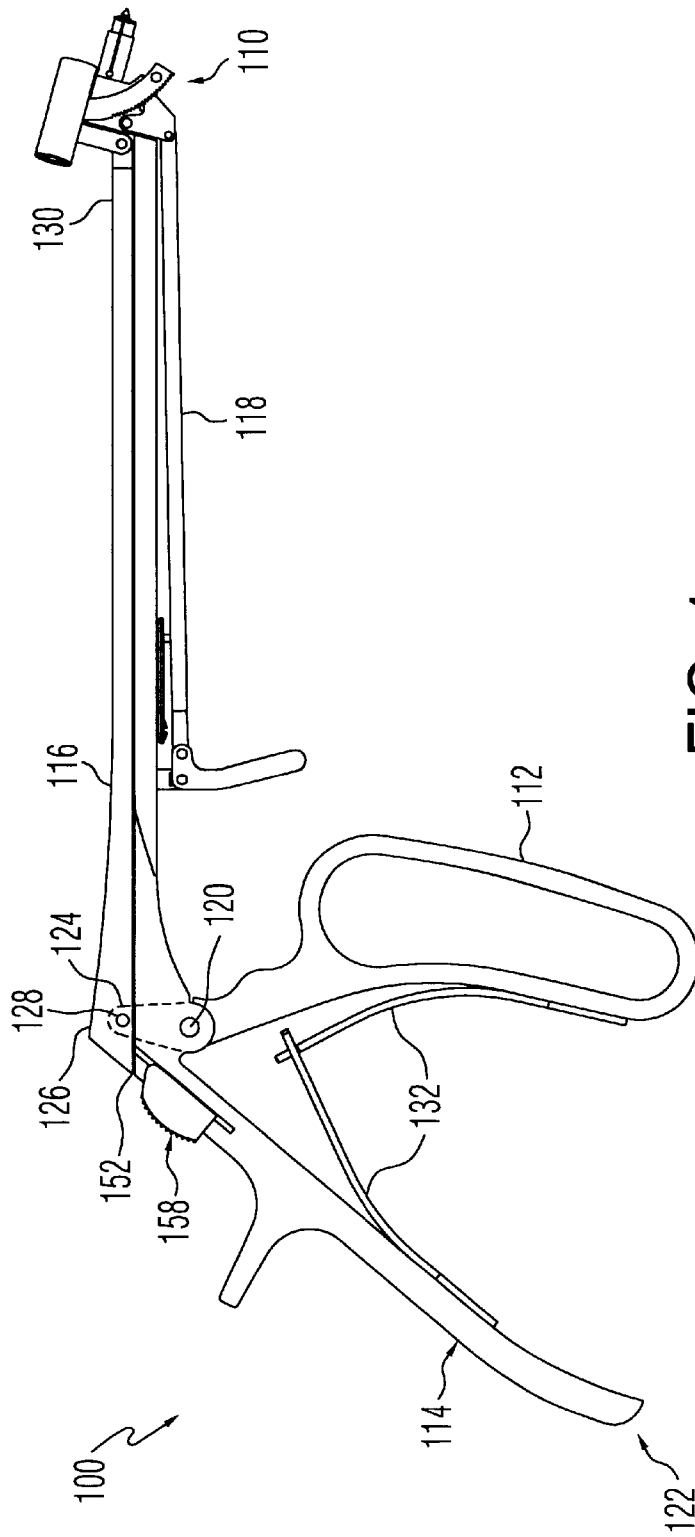
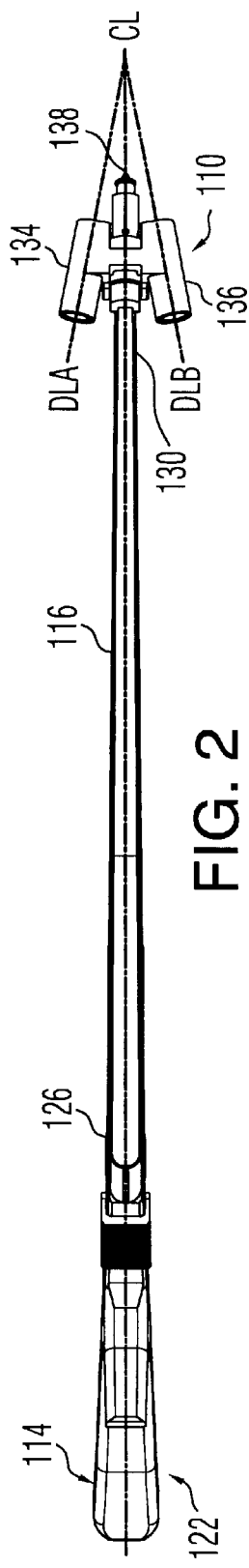
FIG. 1
FIG. 2

REMOTELY ALIGNED SURGICAL DRILL GUIDE

FIELD OF THE INVENTION

The present invention relates to a surgical drill guide and slotted plate that are demountably attachable to each other for retaining a precise alignment therebetween. More particularly, the present invention relates to a surgical drill guide assembly with a plurality of alignment drill tubes that are remotely aligned from respective fastener holes in a bone plate and an expandable bushing that engages a slot in the plate.

BACKGROUND OF THE INVENTION

The use of surgical fixation plates for a variety of orthopedic applications is widely accepted. The plates are used by surgeons to mend, align, and alter compression of patient's bones, and are typically fastened to the bones with a plurality of fasteners such as screws that are installed through holes in the plate. Proper orientation and alignment of fasteners and secure surgical fixation of the plates is crucial to avoiding future complications after implantation.

Locking bone plates used in spinal applications, such as those sold by SYNTHES Spine, must be installed with special care, as the plates are used for long term, intravertebral fixation, bone-fragment fixation, and anterior decompression in the cervical region of the spine. The margin for error in spinal surgery is quite small, particularly because of the sensitivity of the spinal cord and the risk inherent with invasive procedures around the spinal cord. In particular, the dimensions of vertebral bone available for setting fasteners are fairly constrained.

Each fixation plate hole should properly align with its associated screw so that each screw is seated correctly with the plate. Any misalignment of the screw within the plate hole risks tissue damage. In addition, improperly seated screws may result in an unstable or insecure connection of the plate to the bony material, thus potentially defeating the usefullness of the plate. Locking plates, in particular, demand precise fastener alignment. Typical cervical locking plates are generally about 2–3 mm thick, and include screw holes that are inclined by 9° to 15° with respect to the surface of the plate for optimal screw placement in the cervical region of the spine. A variety of types of bone screws are available for securing the plate to the desired anatomical site, such as the expansion-head screws disclosed in U.S. Pat. No. 4,484,570. Surgeons often desire to be able to select the angle at which the screw is installed relative to the plate.

Known drill guides for locking plates, such as disclosed in U.S. Pat. No. 5,851,207, generally include a guide member for guiding a drill bit. A hollow collet is disposed coaxially with the guide member and has a radially expandable forward end with a neck. The neck is configured to press outwardly against an inner wall of a plate hole when the collet is in an expanded position, thereby securing the drill guide to the bone plate. An inconvenience associated with this drill guide is that it includes only one guide member, so the drill guide must be removed and reoriented within each bone plate hole for drilling successive holes in tissue. In addition, after drilling a hole using this drill guide, it must be removed from the plate before a screw can be installed in the hole. Since the expandable collet is inserted within the plate hole, the screw will not fit within the remaining hole diameter. Especially if expansion head screws are used, the full diameter of the plate hole must be free of the drill guide.

The desirability of providing a drill guide that includes more than one guide tube has been recognized. For example, U.S. Pat. No. 5,180,388 discloses an applicator device with two guide tubes attached to a handle. A scale on the handle allows accurate determination of the movement of a drill inserted through the guide tubes and thus the depth of each hole. U.S. Pat. No. 4,714,469 shows another drill guide with an elongated arm having a distal end which is shaped to match the profile of a spinal implant for which the apparatus is to be used. Grooves in the drill guide are adapted to accommodate a drill bit, and linear markings are provided on the surface of the drill guide so that the correct depth for drilling is obtained. U.S. Pat. No. 5,112,336 shows a drill guide and template for use in orthopedic surgery, comprising a template and handle connected by a lockable universal joint. The template is provided with pins so that the template can be set into bone. The pins prevent the template from moving while bores are being made in the bone. Drill bores are provided in the template to conform to a selected prosthesis which the surgeon intends to implant. Despite these drill guide developments, none meets the demands of surgeons working with bone plates, since none attach to a bone plate or provide a high degree of adjustability of drill guide orientation with respect to a bone plate.

U.S. Pat. No. 4,465,065 discloses an L-shaped surgical device for the connection of a fractured neck to the shaft of a femur by means of a pre-drilled connector plate. The tool has a grip and connector arm extending at right angles, and the tool and plate are interconnected by means of a long screw which passes through a longitudinal bore along the connector arm into a tapped hole in the top of the fixator plate. Two pins firmly attached to the connector arm also engage with corresponding holes in the upper part of the plate. Guide tubes extend through holes in the device to holes in the plate. The guide tubes do not permit dynamic angulation of the drilling axis with respect to the holes in the plate.

U.S. Pat. No. 4,119,092 discloses a method of reduction of bone fractures wherein two segments of a broken bone are drawn together by means of a plate extending across both segments. The plate has apertures and a longitudinally disposed chamfered slot. A block with a cross sectional shape similar to the slot is temporarily fitted to the plate, and a hole is drilled in the bone by using a through bore in the block as a guide for the introduction of a drill bit. Again, the block has a fixed drilling axis with respect to the plate.

U.S. Pat. No. 5,676,666 discloses a cervical plate holder/guide clamp that is a modified fixation forceps, and includes a handle, pivot joint, and blades. Each blade includes a guide head with opposing lips which attach to a plate. Guide cylinders are slidably positionable in each guide head and are pushed down to contact with the openings in the plate. The opposing lips contact the outer periphery of the plate. The clamp is used to drill pilot holes; bone screws are inserted in the holes, and then a plate is positioned over the screws with a locking cap affixed to each screw to lock the cervical plate to the screws. Thus, the plate holder/guide clamp disclosed in this patent does not allow the plate to be secured to vertebrae without disengaging the clamp from the plate. Also, the guide cylinders are in contact with the plate, and thus the guide cylinders are not remotely located from the plate to allow screws to be installed while the clamp is engaged with the plate.

U.S. Pat. No. 5,364,399 discloses an anterior cervical plating system. A drill and tap guide assembly is mounted on a fixation plate to provide a firm foundation for accurately drilling and tapping screw holes into the vertebra to be instrumented. The drill and tap guide assembly includes an assembly support which is engaged to the plate by way of a positioning screw and cross pins mounting the positioning screw to the guide body. A tap sleeve and drill guide can then be supported by the assembly support, which both thereby provide accurate positioning for a drill.

U.S. Pat. No. 5,423,826 discloses an anterior cervical plate holder/drill guide. The guide comprises two arms which pivot with respect to each other and a foot attached at the end of each arm. Each foot has a hook which is adapted to securely grasp a spinal plate and a pair of thru-holes. Each hole is aligned with a screw bore in a spinal plate when the guide assembly is engaged to the plate. A number of double-headed fixation pins hold the plate in position against the cervical spine during drilling and tapping. The hook on each foot of the guide attaches to a notch on each end of the plate.

The above-described patents disclose drill guides that have a limited range of orientation adjustment. Furthermore, none can be attached to the bone plate while also providing remote alignment of the drill guides with respect to from the plate. Greater orientation adjustment and more convenient, unobtrusive mounting are therefore desirable and necessary.

SUMMARY OF THE INVENTION

The invention relates to a surgical drill guide assembly comprising at least one alignment drill tube configured to receive and guide a surgical drill bit; a bushing configured to support the at least one alignment drill tube relative to and spaced apart from a bone plate that has a slot and fastener holes, the bushing having a radially expandable forward end; and a drill guide assembly handle coupled to the bushing. The bushing is configured and dimensioned to expand within the bone plate slot to releasably lock the bushing to the bone plate remotely from the bone plate fastener holes.

Advantageously, the radially expandable forward end comprises a plurality of finger portions, and a taper pin slidably received within a guide bore in the bushing is included, with the taper pin being configured and dimensioned to bias the finger portions from a contracted position to an expanded position. The radially expandable forward end of the bushing may be key shaped. Preferably, the radially expandable forward end comprises a shoulder, a neck, and an outwardly projecting rim disposed forward of the neck.

The assembly can also include a variable angle block to which the at least one alignment drill tube is coupled for positioning at a surgeon selected angle with respect to the bone plate. This angle block permits angulation of the at least one alignment drill tube in one plane, and at a range of angulation of about 20°. The variable angle block may be releasably lockable at the surgeon-selected angle.

Preferably, two alignment drill tubes are present, with the bushing disposed along a central axis. Each alignment drill tube has a drilling axis, and all drilling axes are coplanar and converge along the central axis forward of the radially expandable forward end of the bushing. In a preferred arrangement, each alignment drill tube is oriented at an angle of between about 5 and 22° with respect to the central axis.

The assembly may also have a taper pin; an upper actuation bar for slidably positioning the taper pin within the bushing; a variable angle block for angulating the drill tubes at a surgeon selected angle about a central plane; an anchor; and a lower actuation bar for releasably locking the anchor to the variable angle block, thereby maintaining the surgeon selected angle for the drill tubes. A first alignment drill tubes has a first drilling axis, a second alignment drill tube has a second drilling axis, and the first and second alignment drill tubes are preferably positioned such that the drilling axes are converging.

If desired, a latch can be included for releasably maintaining the upper actuation bar in an actuated position. When the expandable forward end of the bushing is key shaped, and the slot in the bone plate has inner walls that define a keyhole shape, the expandable forward end is freely insertable and extractable from the bone plate slot in a contracted position and engages the slot when in an expanded position.

In additional embodiments of the assembly, the taper pin can include a tip for indenting bone. Also, the handle can include a grip that is pivotably connected to a handle member, with the grip being resiliently biased away from the handle member by leaf springs. Furthermore, the bone plate slot can have a wall thickness defined as the distance between a free-side surface and a bone-side surface of the bone plate; and the radially expandable forward end of the bushing comprises a shoulder, a neck, and an outwardly projecting rim disposed forward of the neck so that the neck and rim together span a length that is slightly longer than the thickness of the bone plate slot wall and the rim abuts the bone-side surface of the plate.

BRIEF DESCRIPTION OF THE DRAWINGS

Preferred features of the present invention are disclosed in the accompanying drawings, wherein similar reference characters denote similar elements throughout the several views, and wherein:

FIG. 1 is a side view of a surgical drill guide assembly in accordance with a preferred embodiment of the present invention;

FIG. 2 is a top view of the surgical drill guide assembly of FIG. 1;

DETAILED DESCRIPTION OF THE PREFERRED EMBODIMENTS

Figure 3:
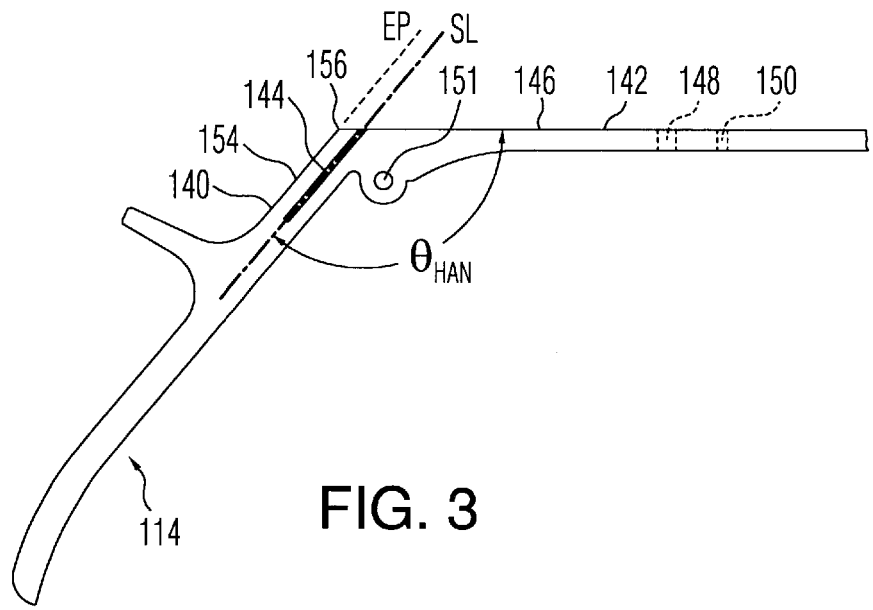
FIG. 3 is a side view of the handle member of the surgical drill guide assembly of FIG. 1.

Referring to FIG. 1, there is shown an exemplary surgical drill guide assembly 100, which is adapted for use with a slotted cervical spine locking bone plate. Assembly 100 includes an alignment device 110, grip 112, and handle member 114, along with upper and lower actuation bars 116, 118, respectively. Handle member 114 and actuation bars 116, 118 are disposed generally parallel to each other. Grip 112 and handle member 114 are pivotably connected by handle pin 120. Together, grip 112 and handle member 114 form a drill guide assembly handle 122, which allows a user to maneuver and use the drill guide assembly. In the preferred embodiment, handle 122 is located remotely from the drilling site, thereby leaving an open space near the locking bone plate. Grip 112 has an arm 124 that extends from handle pin 120 on grip 112 to pivotably attach to a first end 126 of upper actuation bar 116 at actuation pin 128. A second end 130 of upper actuation bar 116 is pivotably attached with alignment device 110. Preferably, leaf springs 132 are fastened to grip 112 and handle member 114 to bias the handle 122 toward a first or open position.

With reference to FIG. 2, drill guide assembly handle 122 and actuation bars 116, 118 (not shown) are disposed along a center plane that contains the center line CL and is perpendicular to the plane of the page. Preferably, alignment device 110 is substantially symmetrical about the center plane. As will be discussed, alignment drill tubes 134, 136, which each may receive and direct the path of a drill bit, are aligned along drilling lines DLA and DLB respectively that converge beyond tip 138. Thus, the features of surgical drill guide assembly 100 permit the surgeon to make a lateral approach from either the left side or right side of the patient. As shown in FIG. 3, handle member 114 has two generally straight sections 140, 142. Section 140 has an upper slotted portion 144 that is disposed along line SL. Preferably, upper slotted portion 144 does not extend all the way through handle member 114. Instead, a second slotted portion is symmetrically disposed about the center plane on the opposite surface of handle member 114. Top surface 146 of section 142 and line SL defining an angle $\theta_{HAN}$. Preferably, angle $\theta_{HAN}$ is about 130° to optimally meet ergonomic considerations, although angles of between 90° and 150° can be used if desired. Mounting holes 148, 150 are provided in section 142. A hole 151 is provided to receive handle pin 120 for connecting grip 112 and handle member 114.

Figure 4:
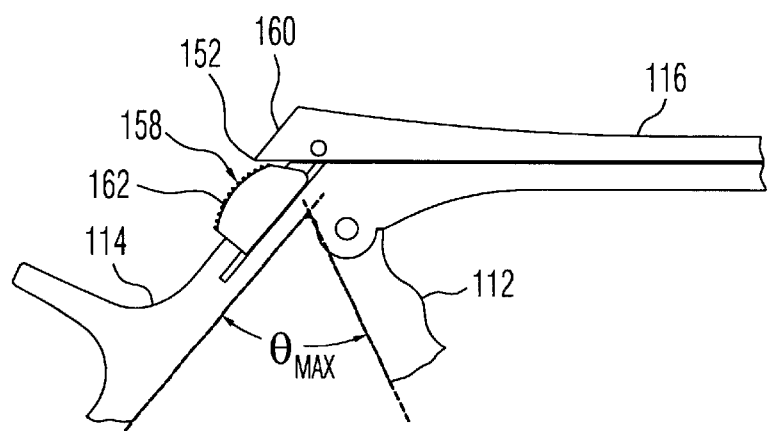
FIG. 4 is a partial side view of the handle of the present invention in the open position.

As shown in FIG. 4, drill guide assembly 100 is in the open position, with grip 112 at maximum separation angle $\theta_{MAX}$ from handle member 114. This open position also corresponds to an unlocked and unactuated state of actuation bar 116, in which vertex 152 of actuation bar 116 is located behind line EP that is generally parallel to line SL and defined along the outer edge 154 of section 140. Thus, in this open position, vertex 152 of actuation bar 116 is located behind vertex 156 of handle member 114, and latch 158 is in a lowered position and thus not engaged with actuation bar 116.

Figure 5:
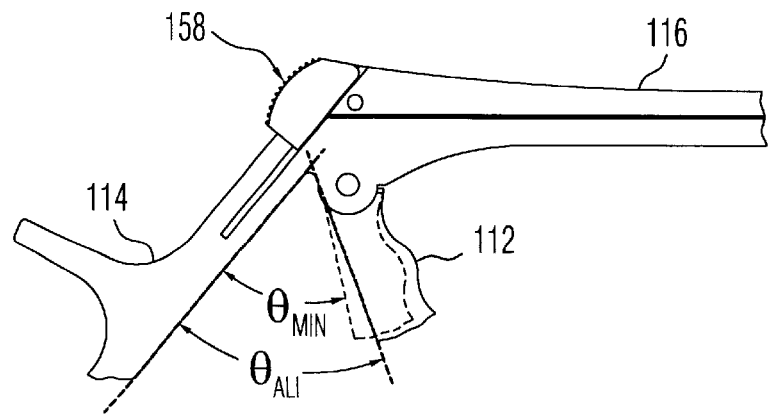
FIG. 5 is a partial side view of the handle of the present invention in the closed position.

When a surgeon squeezes grip 112 toward handle member 114, the arm 124 forces upper actuation bar 116 forward. As shown in FIG. 5, when grip 112 reaches a separation angle $\theta_{ALI}$ from handle member 114, drill guide assembly 100 is in a closed position with actuation bar 116 almost fully actuated. In this position, vertex 152 of actuation bar 116 is generally located along line EP such that side 160 of actuation bar 116 is generally co-linear with edge 154 of section 140.

As leaf springs 132 bias grip 112 and handle member 114 to an open position, a surgeon must continue to squeeze grip 112 and handle member 114 toward each other to maintain an actuated position of actuation bar 116. To facilitate use of surgical drill guide assembly 100, however, a latch 158 may be used to releasably lock upper actuation bar 116 in the almost fully actuated position with grip 112 separated by an angle $\theta_{ALI}$ from handle member 114. This obviates the need for a surgeon to continue to squeeze grip 112 and handle member 114 after proper actuation has occurred. Instead, the surgeon's thumb moves latch 158 into abutment with face 160 of actuation bar 116. Latch 158 remains in place due to the backward pressure applied by face 160 against it.

In a preferred embodiment, the movement of latch 158 is guided along slotted portions 144, with disengagement from slotted portions 144 prevented by an abutment on handle member 114. Alternatively, other means of restricting the travel of latch 158 may be used, such as a protrusion on face 160 of upper actuation bar 116. Preferably, latch 158 is also provided with teeth 162 or ridges to enhance tactile sensation between latch 158 and a surgeon's thumb, thereby facilitating movement of latch 158. Other latch means, such as pins or ratchet mechanisms, may also be used.

Actuation bar 116 is released from the locked position by squeezing grip 112 and handle member 114 to a slightly closer separation angle than $\theta_{ALI}$, such that grip 112 and handle member 114 are separated by an angle $\theta_{MIN}$. Because actuation bar 116 is moved away from latch 158 when separation angle $\theta_{MIN}$ is reached, the backward pressure applied by face 160 against latch 158 is diminished, and latch 158 is freely movable to a position that will not engage upper actuation bar 116.

Advantageously, a surgeon can operate drill guide 100 with only one hand, due to the ergonomic positioning of grip 112 and handle member 114. In embodiments which include latch 158 for releasably locking grip 112 and handle member 114 with respect to each other, latch 158 is also ergonomically positioned so that one handed operation is still convenient.

Figure 6:
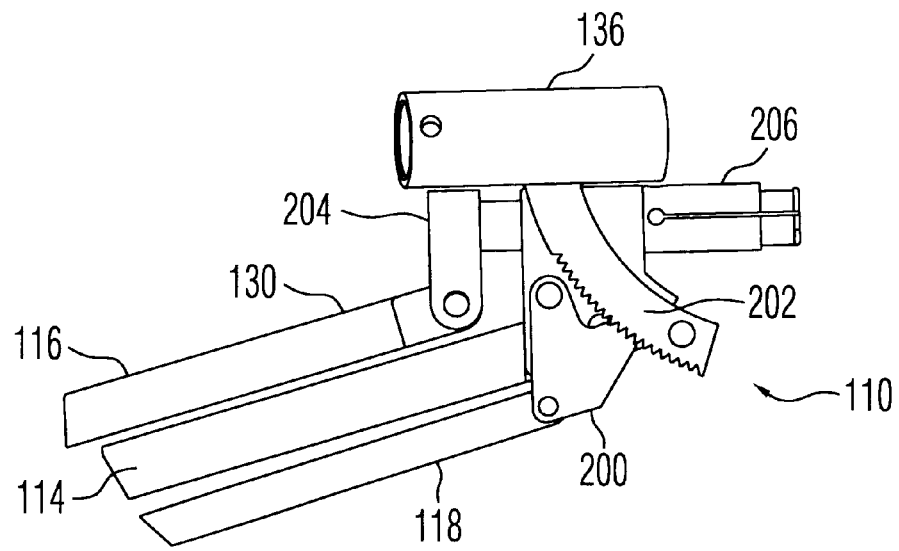
FIG. 6 is a partial side view of the alignment device of the present invention in the open position.
Figure 7:
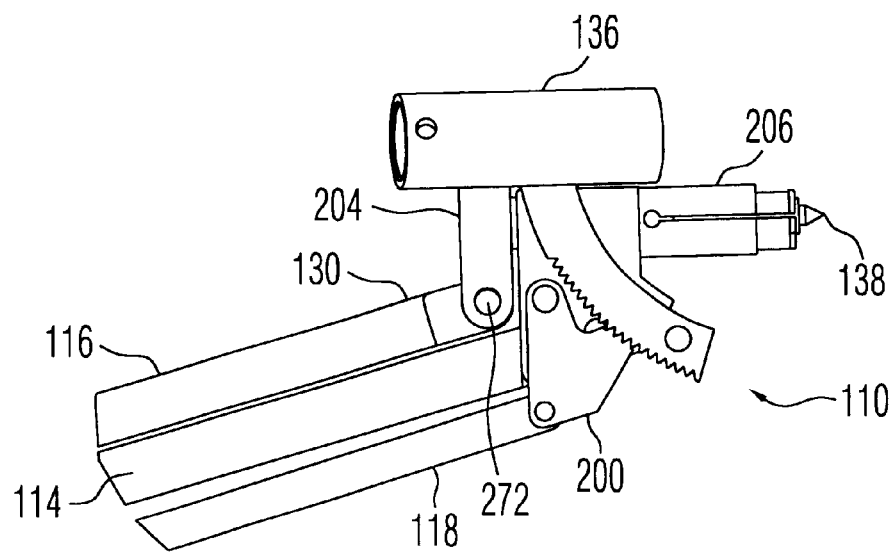
FIG. 7 is a partial side view of the alignment device of the present invention in the closed position.

Turning now to FIGS. 6 and 7, alignment device 110 includes anchor 200, variable angle block 202, taper pin 204, and bushing 206. Alignment device 110 is shown in FIG. 6 with taper pin 204 in a retracted position, which may be achieved when grip 112 and handle member 114 are separated by an angle greater than $\theta_{ALI}$. When the surgeon squeezes handle 112, the taper pin 204 is moved forward within bushing 206, and tip 138 of taper pin 204 emerges from bushing 206 as shown in FIG. 7.

Referring to FIGS. 8–12, bushing 206 coaxially receives taper pin 204 through guide bore 208 about a line 10–10. Preferably, bushing 206 is substantially symmetrical about line 10–10. The forward end 212 of bushing 206 is preferably comprised of longitudinally extending fingers 214. Individual fingers 214 are separated by slits 216 extending longitudinally between adjacent fingers 214. Slits 216 are shown, for example, in FIG. 9, including a circular portion 218 that serves to help minimize stress concentration when fingers 214 are flexed. These fingers 214 are resiliently biased inwardly and naturally assume an inward disposition when in a relaxed state and when the taper pin 204 is in the retracted position. In the preferred embodiment, the inward bias of fingers 214 is selected to produce the desired friction, while allowing operation of handle 122 with only one hand. Alternative resiliency for fingers 214 may be chosen according to the purposes of other embodiments. At a frontmost portion of the expandable forward end 212 of the bushing 206, the fingers 214 form a radially expandable circumferential neck 220. At the back end of and adjacent to neck 220 is a shoulder 222.

In the preferred embodiment, projections that form a radially expandable rim 224 are provided at the front end of and adjacent to neck 220. In alternate embodiments, no rim may be used. For example, in an embodiment without a rim, neck 220 may be tapered with the frontmost portion of neck 220 having a larger diameter than the portion of neck 220 adjacent shoulder 222. Thus, such a tapered neck may expand within a similarly tapered slot or hole in a bone plate, to effectively provide firm alignment of the alignment drill tubes. The several portions of bushing 206, i.e., the neck 220, the shoulder 222, and the rim 224, are preferably a single piece of material of unitary construction.

Side channels 223 are provided on both sides of bushing 206 to direct variable angle block 202. A pin hole 226 is also provided to facilitate the fixing of anchor 200 to bushing 206, and recess 228 is provided to facilitate the fixing of section 142 of handle member 114 to bushing 206.

Figure 8:
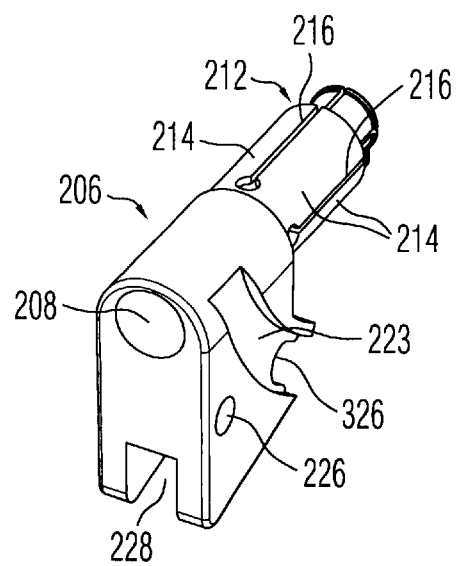
FIG. 8 is a perspective view of the bushing of the surgical drill guide assembly of FIG. 1.
Figure 9:
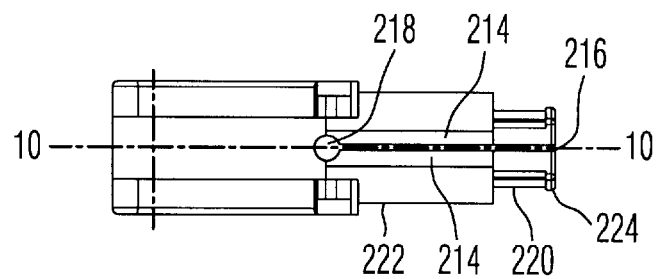
FIG. 9 is a top view of the bushing of FIG. 8.
Figure 10:
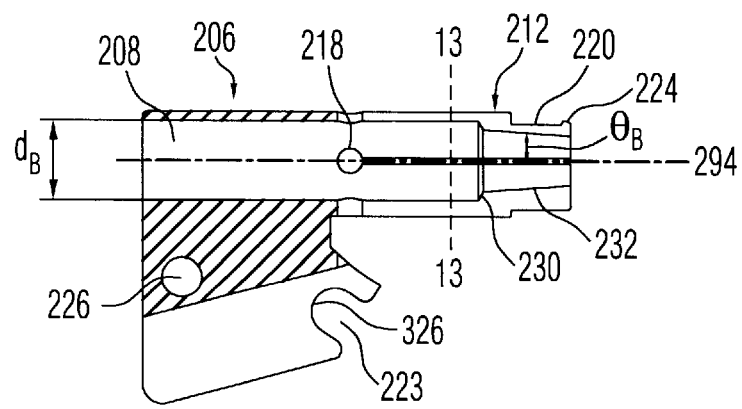
FIG. 10 is a partial cross-sectional view of the bushing of FIG. 9.

In the contracted position shown in FIGS. 8–10, neck 220 and rim 224 of bushing 206 are sized to fit freely through a slot of similar geometry in a bone plate. Notably, because the bushing is configured to engage a slot in the bone plate, rather than the circular holes in the plate through which bone screws are to be inserted, it is possible to drill and tap holes for the bone screws, and insert the bone screws in the drilled holes, without disengaging the surgical drill guide assembly from the bone plate. Referring to FIG. 10, above described bushing 206 is shown in cross-section taken along line 10–10. The inside of the expandable forward end 212 of bushing 206 preferably has a variable inner diameter. Preferably, fingers 214 have a step 230 and a taper 232, resulting in a smaller bushing 206 inner diameter forward of the step 230.

Figure 11:
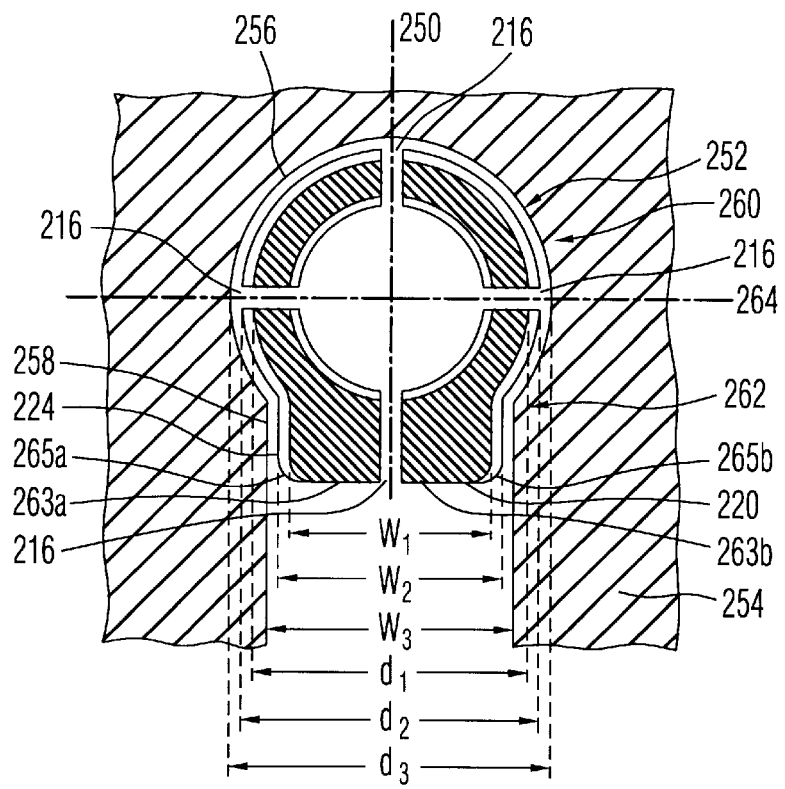
FIG. 11 is a partial back view of the neck and rim of a bushing inserted into the slot of a bone plate.
Figure 12:
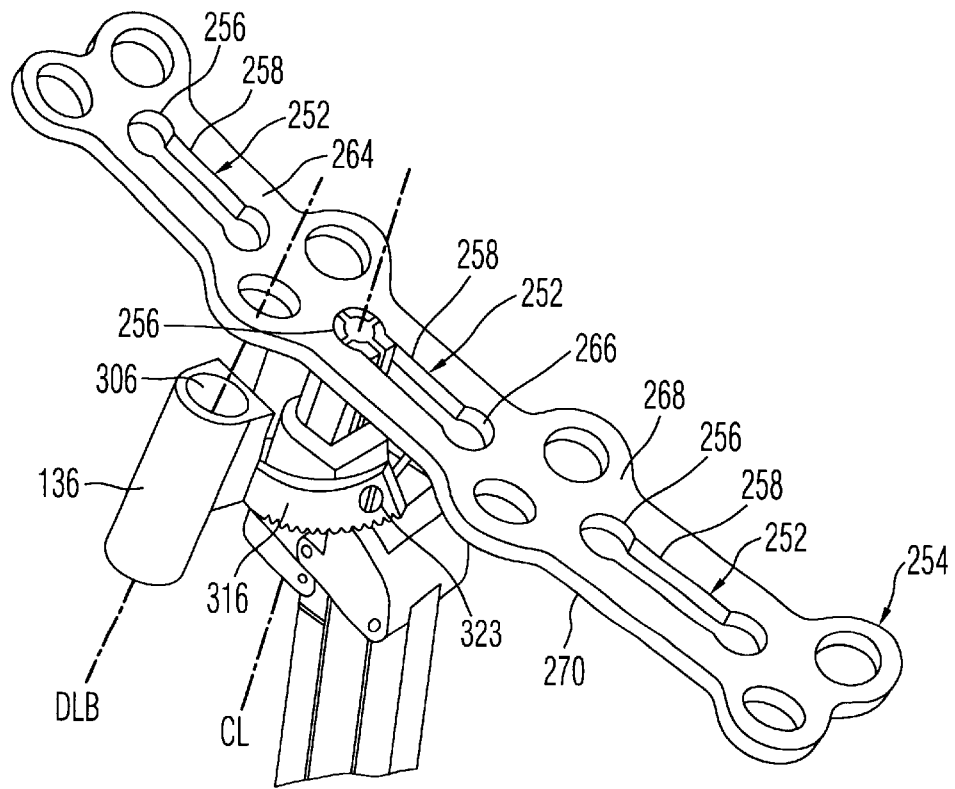
FIG. 12 is a partial perspective view of a surgical drill guide assembly locked to the slot of a bone plate in accordance with a preferred embodiment of the present invention.

As shown in FIGS. 11–12, preferably neck 220 is symmetrically key-shaped about line 250, configured and dimensioned for fitting and expansion within a similarly tapered slot 252 in a bone plate 254. In a preferred embodiment of bone plate 254, slot 252 has at least one rounded portion 256 and a straight portion 258. Preferably, rounded portion 256 has a diameter of about 4.1 mm, and straight portion 258 has a width of about 2.8 mm. The length of straight portion 258 along line 250 may be varied, as long as the length accommodates the dimensions of bushing 206 of surgical drill guide assembly 100.

Bushing 206 is resiliently biased towards the position shown in FIGS. 8–11, in which neck 220 and rim 224 have a contracted size. Preferably, neck 220 has a C-shaped portion 260 and a Y-shaped portion 262, with four quadrants defined by slits 216 along lines 250, 264. C-shaped portion 260 of neck 220 has a contracted neck diameter $d_1$ and the rim has a contracted rim diameter $d_2$. The rounded portion 256 of slot 252 has an inner wall with a slot diameter $d_3$. The contracted rim diameter $d_2$ is smaller than the slot diameter $d_3$ to permit free and unfettered extraction of the rim 224 from the slot 252. Preferably, the contracted rim diameter measures between 0.1 mm and 0.3 mm less than the slot diameter $d_3$. More preferably, the rim diameter $d_2$ is 0.2 mm smaller than the slot diameter $d_3$. The contracted rim diameter $d_2$ is preferably between 3.8 mm and 4.0 mm in a drill guide that functions with a slot diameter $d_3$ of about 4.1 mm. Thus, the contracted rim diameter is at least about 90% and preferably about 94 to 95% of the size of the slot rounded portion. Also, the contracted rim diameter $d_2$ is preferably about between 0.1 mm and 0.2 mm larger than the contracted neck diameter $d_1$. More preferably, the rim 224 protrudes from the neck 220 by a preferred 0.1 mm. Hence, the contracted neck diameter $d_1$ is at least about 90% and preferably about 94 to 95% as large as the contracted rim diameter $d_2$.

The Y-shaped portion 262 of neck 220 has a contracted neck width $W_1$ and the rim has a contracted rim width $W_2$. The straight portion 258 of slot 252 has an inner wall with a slot width $W_3$. The contracted rim width $W_2$ is smaller than the slot width $W_3$ to further permit free and unfettered extraction of the rim 224 from the slot 252. Preferably, the contracted rim width measures between 0.1 mm and 0.3 mm less than the slot width $W_3$. More preferably, the rim width $W_2$ is 0.2 mm smaller than the slot width $W_3$. The contracted rim width $W_2$ is preferably between 2.5 mm and 2.7 mm for use with a plate 254 that has a slot diameter $d_3$ of about 2.8 mm. Thus, the contracted rim width is at least about 90% and preferably about 94 to 95% of the size of the slot width. Also, the contracted rim width $W_2$ is preferably about between 0.1 mm and 0.2 mm larger than the contracted neck width $W_1$. Thus, the rim 224 along the Y-shaped portion 262 protrudes from neck 220 by a preferred about 0.1 mm. Hence, the contracted neck width $W_1$ is at least about 90% and preferably about 94 to 95% as large as the contracted rim width $W_2$.

Notably, because sides 263a, 263b of neck 220 do not contact the walls of slot 252, no rim is provided on sides 263a, 263b. Thus, rounded rim edges 265a, 265b are provided to facilitate insertion and removal of the drill guide within the slot. Preferably, the radius of curvature of the rounded rim edges 265a, 265b is about 0.3 mm. Y-shaped portion 262 must extend an adequate length along line 250 such that sufficient surface contact can be achieved with straight portion 258 of slot 252. Preferably, Y-shaped portion 262 of neck 220 is configured and dimensioned such that portion 262 can have at least about 3 mm of contact with straight portion 258 of slot 252 when neck 220 is expanded.

Those skilled in the art will recognize that the neck and rim of the bushing need not be key-shaped. Other appropriate shapes include a cruciform, T-shape, or figure-eight shape. Such a bushing geometry is appropriately used with at least one correspondingly shaped slot in a bone plate, which is configured and dimensioned to receive the bushing and permit the bushing to lock to the bone plate. In the case of a bone plate with a slot that has a shape that is substantially without a straight section, such as a figure-eight shape, a neck 220 may still be used. Because the transition between the lower straight section and the upper arcuate or V-shaped section in a Y-shaped neck can be formed as a sharp transition, a key-shaped neck 220 may still be used to create an effective locking engagement between a neck 220 and a figure-eight shaped slot. Thus, when a key shaped neck 220 is used in a figure-eight shaped slot, portion 262 of neck 220 need not have significant contact with the walls of the slot. Preferably, the slot also has a shape distinct from the shape of the bone plate fastener holes through which the alignment drill tubes are aimed for drilling of bone screw holes.

The contracted diameters and lengths of neck 220 and rim 224 permit a surgeon to extract, and most preferably also insert, the rim 224 of the bushing 206 through slot 252 without the rim 224 catching in the far side 268 of the plate 254 when bushing 206 is contracted. This arrangement virtually eliminates the possibility of bushing 206 failing to disengage from a bone plate 254. At the same time, having a rim 224 provides the surgeon with a detectable feel for when the rim has completely passed through slot 252. In alternative embodiments, rim 224 may be eliminated completely, for instance by reducing the contracted rim diameter $d_2$ to an equal size as the contracted neck diameter $d_1$, and by reducing the contracted rim width $W_2$ to an equal size as the contracted neck width $W_1$. These embodiments, though, would lack the signal to the surgeon produced by full passage of rim 224 through slot 252. Preferably, to further facilitate free removal of rim 224 from slot 252, the rim 224 is rounded in a cross-section taken parallel to center plane. The cross section preferably curves around a radius of about 0.05 mm.

Figure 13:
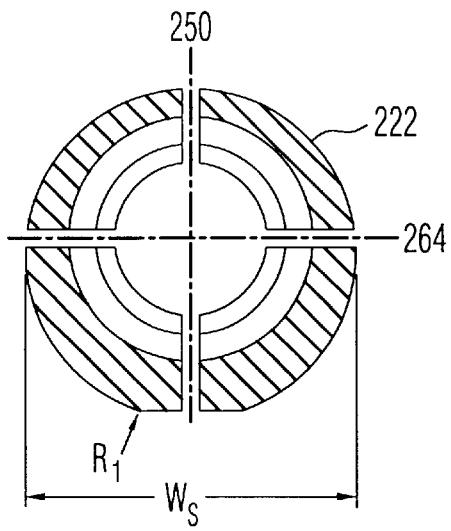
FIG. 13 is a partial cross-sectional view of the shoulder of a bushing of the present invention.
Figure 14:
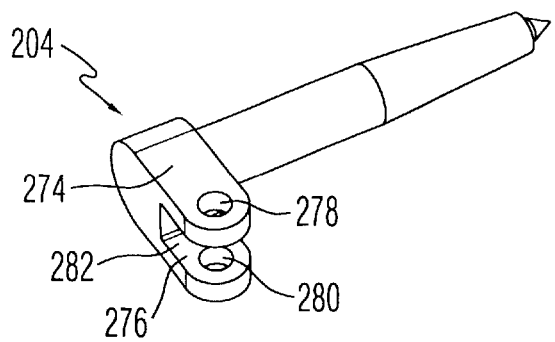
FIG. 14 is a perspective view of the taper pin of the surgical drill guide assembly of FIG. 1.
Figure 15:
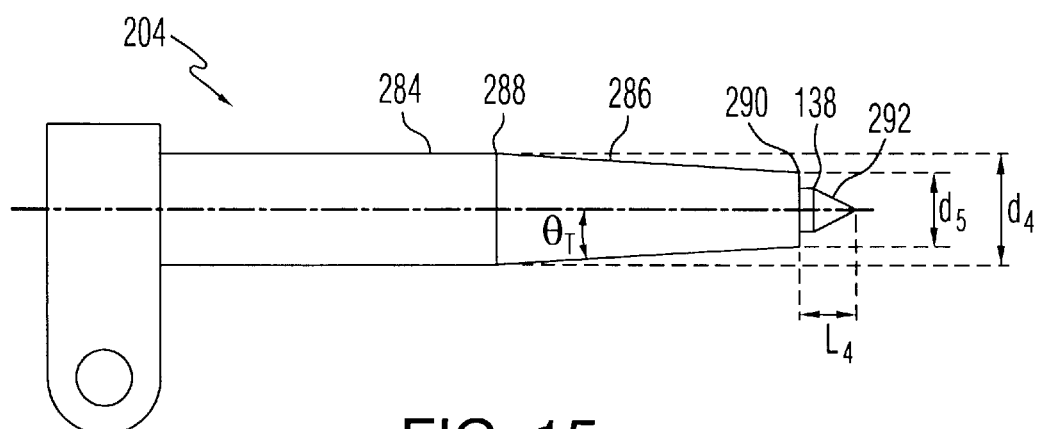
FIG. 15 is a side view of the taper pin of FIG. 14.

Referring to FIG. 13, shoulder 222 is shown in cross-section taken along line 13–13 of FIG. 10. Shoulder 222 has a maximum width $W_S$ taken parallel to line 264 that is greater than the slot diameter $d_3$ such that the shoulder 222 cannot be inserted through slot 252. Still further, shoulder 222 has a maximum radius of curvature $R_1$ such that the shoulder 222 cannot be inserted through slot 252.

In the preferred embodiment, neck 220 together with rim 224 span a length that is slightly longer than the thickness of the slot wall 266 from the bone-side surface 268 to the free-side surface 270 of plate 254. Thus, the neck can abut the wall of the locking bone plate slot and the rim 224 can abut the bone-side surface 268 of a plate 254. In this manner, the drill guide assembly can be secured to the plate 254, restricting relative movement.

As shown in FIGS. 6–8 and 14–15, taper pin 204 is configured and dimensioned to be slidably received within guide bore 208 of bushing 206. Preferably, taper pin 204 is coupled to actuation bar 116 with a pin 272 that extends through a bore in actuation bar 116. Parallel and symmetrical flanges 274, 276, with holes 278, 280 respectively, together define a gap 282 that receives actuation bar 116. Once the bore in the second end 130 of upper actuation bar 116 is aligned with the flange holes 278, 280, the pin 272 may be inserted therein to couple the taper pin 204 to actuation bar 116.

Taper pin 204 extends through guide bore 208. Tip 138 of taper pin 204 is housed fully within guide bore 208 except when actuation bar 116 is actuated such that tip 138 emerges from bushing 206. In the preferred embodiment, a cylindrical section 284 and a tapered, conical section 286 are provided on taper pin 204 to facilitate movement of taper pin 204 within guide bore 208. Cylindrical section has a diameter $d_4$, while conical section 286 tapers from a diameter $d_4$ at the transition 288 to a diameter $d_5$ at end 290. Preferably, the diameter $d_4$ measures between 0.1 mm and 0.3 mm less than the maximum diameter $d_B$ of guide bore 208, as indicated in FIG. 10. Most preferably, diameter $d_4$ is 0.1 mm smaller than diameter $d_B$. The diameter $d_4$ is preferably about 4.0 mm, for guiding a taper pin 204 with a maximum diameter $d_4$ of about 3.9 mm and a diameter $d_5$ of about 2.6 mm at end 290. Thus, the taper angle $\theta_T$ of conical section 206 preferably is about 3.5°.

Tip 138 of taper pin 204 preferably includes a conical portion 292. When bushing 206 is placed in slot 252 of plate 254, and actuation bar 116 is actuated such that the almost fully actuated position is reached (i.e. when grip 112 is separated by an angle $\theta_{ALI}$ from handle member 114), tip 138 protrudes beyond rim 224 of bushing 206 and slightly indents the bone below plate 254. As tip 138 is slightly driven into the bone, the tip provides anchoring and guidance for the alignment of bushing 206 until a positive lock with plate 254 has been achieved. Advantageously, tip 138 also provides anchoring of the bone plate 254 and drill guide assembly 100 until at least one screw has been installed to fix the plate to the bone. Because of the small size of tip 138, tissue irritation is minimized. Preferably, tip 138 has a length $L_4$ of about 2 mm.

Alternate embodiments of taper pin 204 do not include a tip 138, thereby virtually eliminating the tissue irritation that may result from use of drill guide assembly 100 to install a bone plate. In addition, other shapes of taper pins may be used, such as a non-tapered cylindrical pin or a pin with a spherical protrusion at its front end. Furthermore, in embodiments of drill guide assembly 100 that have a bushing without a rim, and a taper pin without a protruding tip, the slot in the bone plate need not necessarily be a through-slot. Thus, the slot need only be a channel in the plate. In addition, the channel walls may be contoured to facilitate positive locking of the bushing to the plate. In another alternate embodiment, a rim may be provided on the bushing, and may be configured and dimensioned to fit within a groove formed on in the internal surface of the slot or in the channel walls.

Taper pin 204 and bushing 206 cooperate to permit drill guide assembly 100 to lock to a bone plate. The conical section 286 of taper pin 204 cooperates with the fingers 214 to expand the fingers 214 when the taper pin 204 is moved into a locked position. The conical section 286 of taper pin 204 pushes outwardly against the inner surface of bushing 206 as the taper pin 204 is moved forward to expand the forward end 212 of bushing 206. In this embodiment, the conical section mates with and pushes against the inner surface of bushing 206 forward of circular portion 218 of slits 216 in fingers 214, to push the fingers 214 radially outward.

When the taper pin 204 is in the unlocked position as shown in FIG. 6, the conical section 286 allows fingers 214 to return to a relaxed, contracted position. This allows bushing 206 to be inserted and retracted from the plate slot. The inner surface of the bushing 206 forward of step 230 is preferably tapered at an angle $\theta_B$ to line 294 that is about 1° more than taper angle $\theta_T$ of conical section 286, and preferably angle $\theta_B$ is about 4°. A desirable amount of movement of taper pin 204 within bushing 206 is thus provided to bias fingers 214 of bushing 206 from a contracted position to an expanded position. Alternative taper angles of conical section 286 and inner surfaces of bushing 206 may be chosen according to the purposes of other embodiments. In addition, a preferred, short travel of scissor grip 112 is required to expand and contract fingers 214 of bushing 206.

Before and during locking bone plate implantation, the surgeon may insert the expandable forward end 212 of bushing 206, in particular neck 220 and rim 224, into a slot 252 in a bone plate 254. By squeezing handle 122, the surgeon may grasp and manipulate the plate 254 without an additional plate holder if he or she so desires. Preferably, friction between the forwardly moved conical section 286 of taper pin 204 and the inner surface of fingers 214 especially at neck 220 and rim 224 retains the expandable forward end 212 of bushing 206 in an expanded, locked position. Thus, when bushing 206 is in the expanded, locked position in slot 252 of a plate 254 placed against the cervical vertebrae, plate motion during the drilling operation can be minimized. Plate motion may be additionally minimized by the additional use of a taper pin 204 having a tip 138, as the tip slightly depresses the vertebrae and thus serves an anchoring function.

Figure 16:
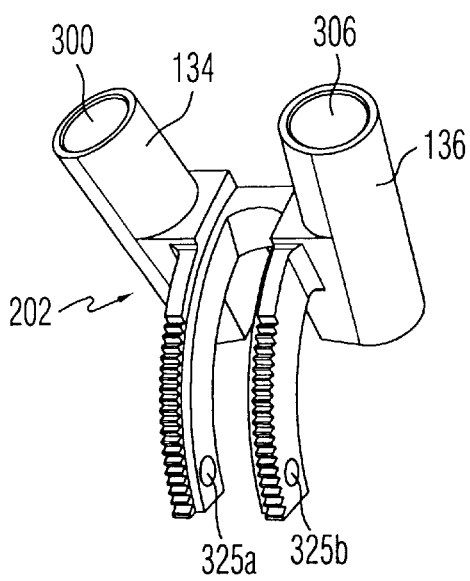
FIG. 16 is a perspective view of the variable angle block of the surgical drill guide assembly of FIG. 1.
Figure 17:
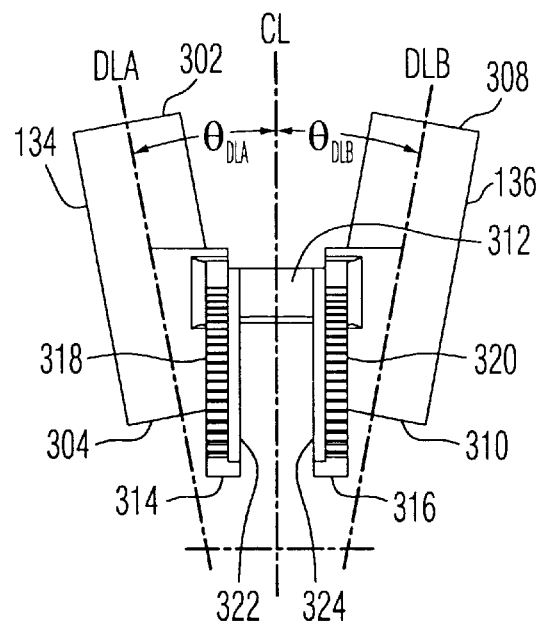
FIG. 17 is a front view of the variable angle block of FIG. 16.
Figure 18:
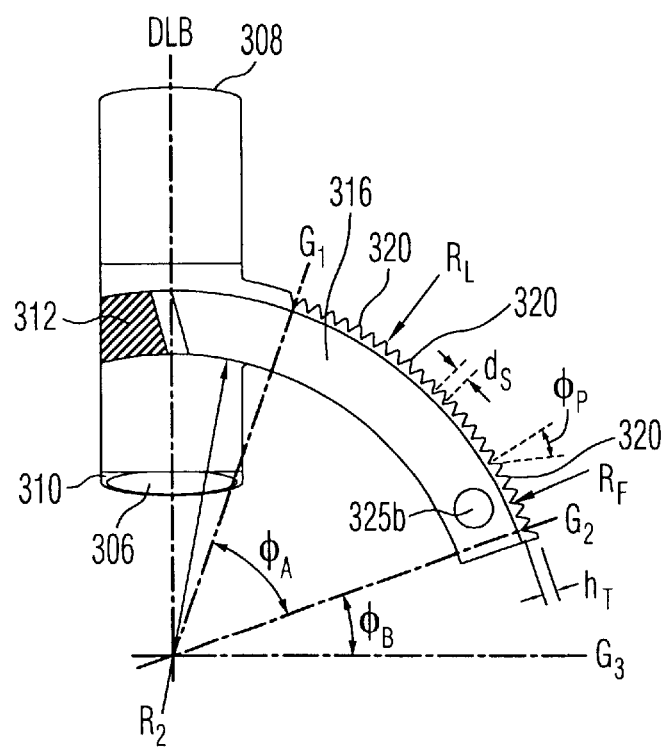
FIG. 18 is a partial cross-sectional side view of the variable angle block of FIG. 17.
Figure 19:
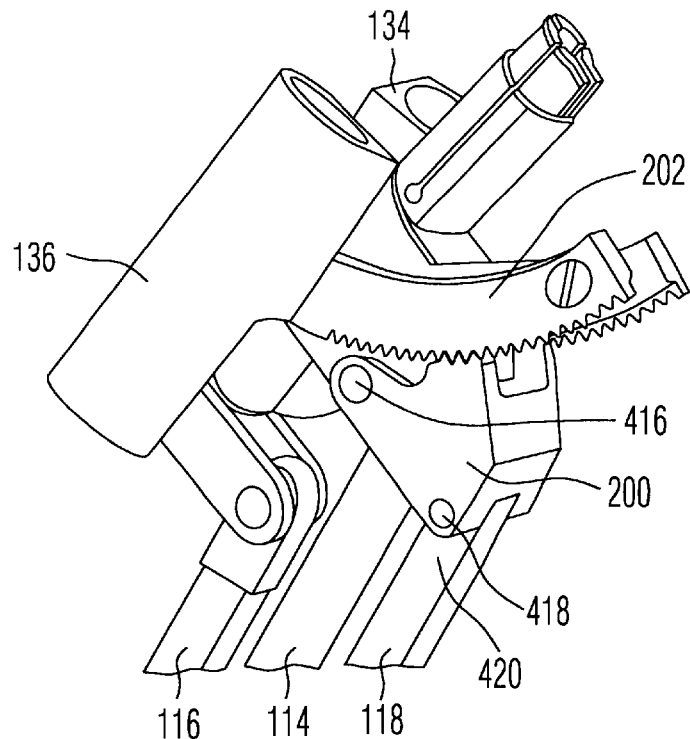
FIG. 19 is another perspective view of a surgical drill guide assembly in accordance with a preferred embodiment of the present invention.
Figure 20:
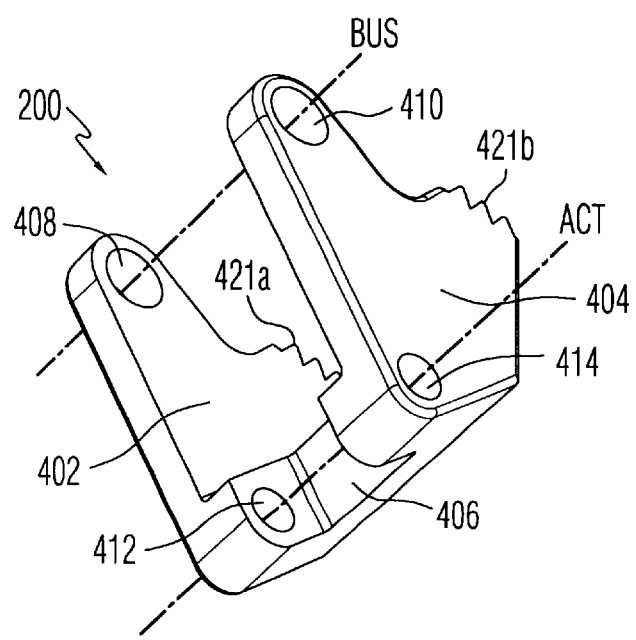
FIG. 20 is a perspective view of the anchor of the surgical drill guide assembly of FIG. 1.
Figure 21:
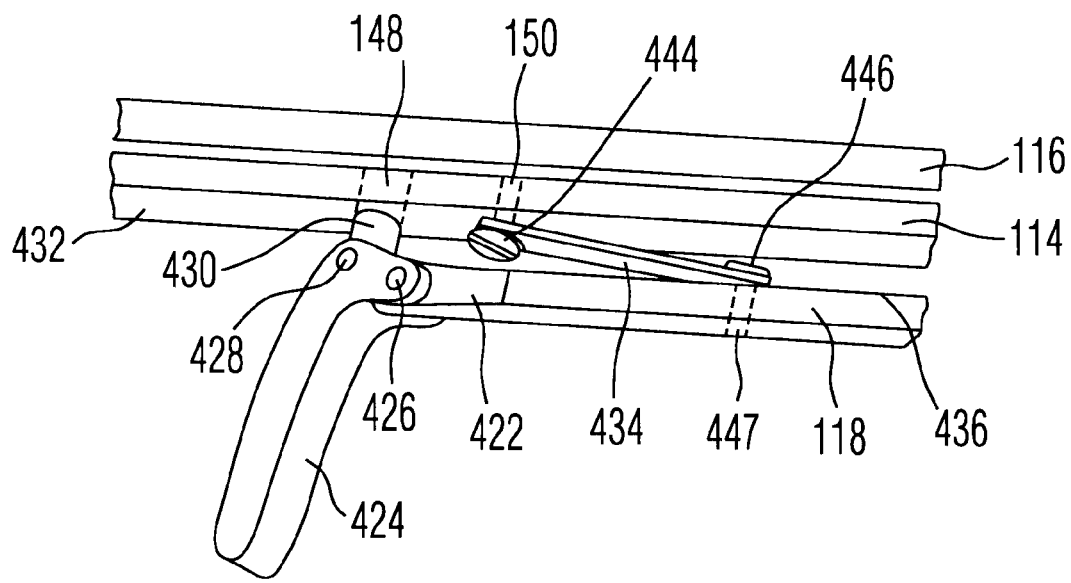
FIG. 21 is a perspective view of the lower actuation bar, lever, and bent spring of a surgical drill guide assembly in accordance with a preferred embodiment of the present invention.

Turning now to FIGS. 16–18, variable angle block 202 includes alignment drill tubes 134, 136. In the preferred embodiment, two alignment drill tubes are provided. Alternatively, variable angle block 202 may include more than two alignment drill tubes.

A bore 300 aligned along drilling line DLA extends through alignment drill tube 134, and connects upper surface 302 and lower surface 304. Similarly, a bore 306 aligned along drilling line DLB extends through alignment drill tube 136, and connects upper surface 308 and lower surface 310. Bores 300, 306 are configured to receive a surgical drill bit, with bore upper surfaces 302, 308 serving as stops that limit the travel, for example, of a surgical drill bit secured in a chuck. Thus, each bore 300, 306 is sized to retain a spinning bit in a precise coaxial alignment with drilling lines DLA, DLB respectively. Preferably, bores 300, 306 each have a generally constant internal diameter of about 5.8 mm.

Drill tubes 134, 136, and bores 300, 306 respectively, are aligned such that drilling lines DLA, DLB converge in a direction from upper surfaces 302, 308 to lower surfaces 304, 310 respectively. Moreover, drill tubes 134, 136 preferably have a fixed orientation with respect to the center plane, such that the angular separation $\theta_{DLA}$ between drilling line DLA and the center plane is equal to the angular separation $\theta_{DLB}$ between drilling line DLB and the center plane. Angular separations $\theta_{DLA}$, $\theta_{DLB}$ are each between about 5 and 22°, preferably between 10° and 11°, and most preferably 10.5°. Advantageously, the fixed medial convergence of the drilling lines DLA, DLB makes the drilling and screw implantation process predictable, inasmuch as the risk of one screw hitting the other screw during implantation is significantly diminished. Furthermore, the insertion of the screws convergent toward the sagittal plane provides better fixation to the bone and concomitant resistance to screw backout. Drill tubes 134, 136 are preferably sized so that once plate 254 is properly positioned over the implantation site and bushing 206 is locked to the plate, drill tubes 134, 136 are positioned at a distance beyond the patient's body such that a spinning surgical drill bit will not laterally reach or harm surrounding tissues that the surgeon does not intend to drill.

Preferably, the surgical drill bits used with surgical drill guide assembly 100 are configured and dimensioned to drill holes of about 12, 14, or 16 mm in depth. Suitable drill bits typically have integral stops so that when the drill bits are used with alignment drill tubes of an established length, the holes produced by the drill bits will not be deeper than the intended depth using a given bit. The stops may be positioned to abut the upper surfaces 302, 308 of alignment drill tubes 134, 136 respectively when drill bits have been inserted in the tubes to a particular depth.

In the preferred embodiment, variable angle block 202 also includes bridge member 312, which joins outer surfaces of drill tubes 134, 136, as well as angulation arms 314, 316 with teeth 318, 320 respectively. Variable angle block 202 is preferably symmetrical about the center plane. Shoulder portions 322, 324 of angulation arms 314, 316 respectively are accommodated within side channels 223 on the sides of bushing 206. Shoulder portions 322, 324 ride smoothly within the side channels, thereby guiding and facilitating the orientation of variable angle block 202. Referring to FIG. 18, there is shown a cross section of variable angle block 202 taken along the center plane. Preferably, teeth 320 have a separation $d_S$ of about 0.77 mm, a pressure angle $\phi_P$ of 30°, a whole depth $h_T$ of about 0.71 mm, a fillet radius RF of no more than about 0.1 mm, and a top land radius $R_L$ of about 0.1 mm. Furthermore, the separation angle $\phi_A$ between lines G1, G2 is preferably about 50.6°, while the separation angle $\phi_B$ between lines G2 and G3 is preferably about 20°. It should be noted that drilling line DLB is perpendicular to line G3.

As best seen in FIGS. 8, 10, 12, and 16–18, a shaft screw 323 is inserted within holes 325a, 325b of angulation arms 314, 316 respectively to connect the angulation arms 314, 316. The range of movement of variable angle block 202 is thus limited, because bridge member 312 and lower channel surface 326 together prevent variable angle block 202 from being removed from bushing 206. Thus, shoulder portions 322, 324 ride within the side channels 223 of bushing 206, allowing a limited range of angulation of variable angle block 202. Preferably, variable angle block 202 is free to move over a range of about 20° in a single plane, most preferably in the cephalad/caudal plane. Notably, a surgeon may reset the angulation of variable angle block 202 after drilling or tapping each hole and/or inserting each bone screw. Thus, surgical drill guide assembly 100 permits the surgeon the freedom to vary the angulation for drilling of each hole and insertion of each screw. The surgeon therefore has greater flexibility when faced with awkward bone geometries or damaged bone regions.

Referring to FIGS. 19–22, means are shown by which variable angle block 202 may be locked at a particular amount of angulation. In the preferred embodiment, anchor 200 has side portions 402, 404 connected by a middle portion 406 therebetween. The side portions 402, 404 are symmetrically disposed about lower actuation bar 118, and thus also about the center plane. Each side portion 402, 404 has a pair of holes provided therethrough. A first set of holes 408, 410 are coaxially aligned about axis BUS, while a second set of holes 412, 414 are coaxially aligned about axis ACT. Sides 402, 404 are preferably positioned on the outer surface of bushing 206, such that holes 408, 410 are aligned with coaxial holes 226 on both sides of bushing 206. A pin 416 is inserted through holes 408, 410, and holes 226, such that anchor 200 is pivotably connected to variable angle block 202. The second set of holes 412, 414 are coaxially aligned with a bore (not shown) through lower actuation bar 118, and a pin 418 is inserted through the bore such that anchor 200 is pivotably connected to lower actuation bar 118 at end 420.

Figure 22:
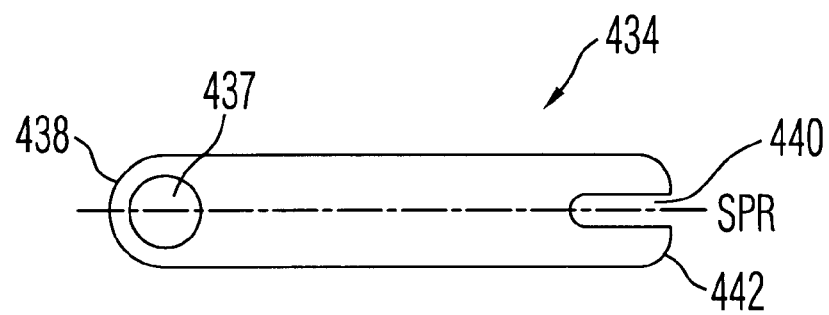
FIG. 22 is a top view of the bent spring of FIG. 21.

End 422 of lower actuation bar 118 is pivotably connected to trigger 424 by pin 426. In turn, trigger 424 is pivotably connected to handle member 114 by pin 428, and pin 428 extends through a bore in a post 430 extending from the bottom surface 432 of handle member 114. Preferably, post 430 is secured to handle member 114 through hole 148. In addition, a bent spring 434 extends between bottom surface 432 of handle member 114 and top surface 436 of lower actuation bar 118. As shown in FIG. 22, a bore 437 extends through bent spring 434 at a first end 438, while a through-slot 440 is formed in bent spring 434 at a second end 442.

Bore 437 and through-slot 440 are thus coaxially located about axis SPR at opposite ends of bent spring 434. Preferably, bent spring 434 is fixed to bottom surface 432 of handle member 114 using a fastener 444 such as a screw extending through bore 437 in bent spring 434 and hole 150 in handle member 114. An untightened screw 446 or other post means is mounted through top surface 436 of lower actuation bar 118 within hole 447, and is received within through-slot 440 of bent spring 434. Screw 446 is located such that even when lower actuation bar 118 has not been actuated, the movement of bent spring 434 is still constrained by screw 446 to movement along axis SPR. Bent spring 434 is slightly curved about axis SPR.

Bent spring 434 biases lower actuation bar 118 to an actuated position, in which anchor 200 is pivoted about pin 418 and teeth 421a, 421b on anchor 200 are engaged with teeth 318, 320 respectively on variable angle block 202. This engagement fixes the angulation chosen by the surgeon for variable angle block 202, and in particular the angulation of drill tubes 134, 136 for guiding surgical drill bits. To disengage teeth 421a, 42b from teeth 318, 320 respectively, the surgeon pulls trigger 424 toward straight section 140 of drill guide assembly handle 122, thereby pivoting teeth 421a, 421b of anchor 200 away from teeth 318, 320 on variable angle block 202. As trigger 424 pivots about pin 428, lower actuation bar 118 is translated toward handle member 114. The angulation of variable angle block 202 may then be set, and when the surgeon releases trigger 424, bent spring 434 returns anchor 200 to engagement with variable angle block 202.

Preferably, the components of surgical drill guide assembly 100 are metallic, passivated, and electropolished. Most preferably, the components are formed of stainless steel, except for the springs which are formed of spring steel. Preferably, at least the handle member is forged, while the other components are machined, and the surgical drill guide assembly preferably has a matte finish so that the surfaces of the components do not reflect operating room light in such a manner as to distract the surgeon. Some components may be subjected to heat treatments so that the surfaces are work hardened. The surfaces are preferably burr-free. Thus, such a surface finish allows individual components to move with respect to each other in a smooth and non-binding fashion through each component's entire range of motion. Additionally, all pins and fasteners are preferably flush with the surfaces into which they are fixed, with the exception of fasteners 444, 446.

The present invention also involves a method of drilling holes in cervical vertebra. A surgeon inserts the bushing of a surgical drill guide assembly into a plate slot and squeezes the handle to slide the taper pin forward, expanding the bushing with the conical portion of the taper pin and locking the drill guide assembly to the plate. The surgeon then releasably locks the bushing to the plate by locking the taper pin and bushing in fixed relation to each other, thereby relieving the surgeon of the need to squeeze the handle. The plate is positioned on top of a bone. The surgeon angulates the alignment drill tubes that receive the surgical drill bit to a desired angulation, and locks the alignment drill tubes at the desired angulation. The surgeon aligns the surgical drill bit along the drilling axis defined through the center of the bore in the first alignment drill tube and inserts the drill bit in the tube. The surgeon then drills a first hole coaxial with the central axis of a first fastener hole in the plate. The surgeon then aligns the surgical drill bit along the drilling axis defined through the center of the bore in the second alignment drill tube and inserts the drill bit in the tube. The surgeon then drills a second hole coaxial with the central axis of a second fastener hole in the plate. The holes may be tapped using taps that are extended through the alignment drill tubes. Each bone screw may be installed in a fastener hole in the bone plate while extending a suitable instrument, along with the bone screw, through an alignment drill tube. He or she unlocks the bushing from the plate, opens the handle of the drill guide to contract the bushing from the slot, and then freely and unfetteredly removes the drill guide assembly from the plate.

While the invention has been shown and described herein with reference to particular embodiments, it is to be understood that the various additions, substitutions, or modifications of form, structure, arrangement, proportions, materials, and components and otherwise, used in the practice of the invention and which are particularly adapted to specific environments and operative requirements, may be made to the described embodiments without departing from the spirit and scope of the present invention. For example, the surgical drill guide assembly may have alignment drill tubes that can be singly or together angulated in the sagittal plane, thereby permitting a range of convergence angles to be chosen for the holes to be drilled and further permitting a range of spacings of plate holes to be accommodated. Moreover, alignment drill tubes that are demountably attachable to the variable angle block may be provided so that a surgeon may select alignment drill tubes with holes that precisely accommodate a desired drill bit size. In addition, the handle member may include a grip that generally follows the contours of fingers that hold the grip. The presently disclosed embodiments are therefore to be considered in all respects as illustrative and not restrictive, the scope of the invention being indicated by the appended claims, and not limited to the foregoing description.

What is claimed is:

1. A surgical drill guide assembly comprising:
   at least one alignment drill tube configured to receive and guide a surgical drill bit;
   a bushing configured to support the at least one alignment drill tube relative to and spaced apart from a bone plate that has a slot and fastener holes, the bushing having a radially expandable forward end; and
   a drill guide assembly handle coupled to the bushing;
   wherein the bushing is configured and dimensioned to expand within the bone plate slot to releasably lock the bushing to the bone plate remotely from the bone plate fastener holes, and wherein at least one of the at least one alignment drill tube is aligned with a corresponding fastener hole.

2. The surgical drill guide assembly of claim 1, wherein the radially expandable forward end comprises a plurality of finger portions.

3. The surgical drill guide assembly of claim 2, further including a taper pin slidably received within a guide bore in the bushing, with the taper pin being configured and dimensioned to bias the finger portions from a contracted position to an expanded position.

4. The surgical drill guide assembly of claim 2, wherein the radially expandable forward end is key shaped.

5. The surgical drill guide assembly of claim 1, further including a variable angle block to which the at least one alignment drill tube is coupled for positioning at a surgeon selected angle with respect to the bone plate.

6. The surgical drill guide assembly of claim 5, wherein the variable angle block permits angulation of the at least one alignment drill tube in one plane.

7. The surgical drill guide assembly of claim 6, wherein the range of angulation is about 20°.

8. The surgical drill guide assembly of claim 6, wherein the variable angle block is releasably lockable at the surgeon-selected angle.

9. The surgical drill guide assembly of claim 1, wherein the radially expandable forward end comprises a shoulder, a neck, and an outwardly projecting rim disposed forward of the neck.

10. The surgical drill guide assembly of claim 1 wherein two alignment drill tubes are present.

11. The surgical drill guide assembly of claim 10, wherein the bushing is disposed along a central plane, each alignment drill tube has a drilling axis, and all drilling axes are coplanar and converge along the central plane forward of the radially expandable forward end of the bushing.

12. The surgical drill guide assembly of claim 11, wherein each alignment drill tube is oriented at an angle of between about 5 and 22° with respect to the central axis.

13. The surgical drill guide assembly of claim 10, further comprising:
a taper pin;
an upper actuation bar for slidably positioning the taper pin within the bushing;
a variable angle block for angulating the drill tubes at a surgeon selected angle about a central plane;
an anchor; and
a lower actuation bar for releasably locking the anchor to the variable angle block, thereby maintaining the surgeon selected angle for the drill tubes.

14. The surgical drill guide assembly of claim 13, wherein a first alignment drill tube has a first drilling axis, a second alignment drill tube has a second drilling axis, and the first and second alignment drill tubes are positioned such that the drilling axes are converging.

15. The surgical drill guide assembly of claim 13, further comprising a latch for releasably maintaining the upper actuation bar in an actuated position.

16. The surgical drill guide assembly of claim 15, wherein the expandable forward end of the bushing is key shaped, and the slot in the bone plate has inner walls that define a keyhole shape, the expandable forward end being freely insertable and extractable from the bone plate slot in a contracted position and engaging the slot when in an expanded position.

17. The surgical drill guide assembly of claim 13, wherein the taper pin further includes a tip for indenting bone.

18. The surgical drill guide assembly of claim 13, wherein the drill guide assembly handle is comprised of a grip pivotably connected to a handle member, the grip being resiliently biased away from the handle member by leaf springs.

19. The surgical drill guide assembly of claim 10, wherein:
the bone plate slot has a wall thickness defined as the distance between a free-side surface and a bone-side surface of the bone plate; and
the radially expandable forward end of the bushing comprises a shoulder, a neck, and an outwardly projecting rim disposed forward of the neck;
wherein the neck and rim together span a length that is slightly longer than the thickness of the bone plate slot wall and the rim abuts the bone-side surface of the plate.

20. A surgical drill guide assembly comprising:
a plurality of alignment drill tubes each configured to receive and guide a surgical drill bit, the alignment drill tubes held spaced apart from a bone plate that has a slot and fastener holes;
a bushing having a radially expandable forward end; and
a drill guide assembly handle coupled to the bushing;
wherein the bushing is configured and dimensioned to expand within the bone plate slot to releasably lock the bushing to the bone plate remotely from the bone plate fastener holes.

* * * * *